US010588981B2

(12) United States Patent
Celia, Jr.

(10) Patent No.: US 10,588,981 B2
(45) Date of Patent: Mar. 17, 2020

(54) DIE PLACEMENT HEAD WITH TURRET (71) Applicant: MRSI Systems, LLC, N Billerica, MA (US)

(72) Inventor: Nicholas Samuel Celia, Jr., Avon, MA (US)

(73) Assignee: MRSI Systems LLC, Tewksbury, MA (US)

( * ) Notice: Subject to any disclaimer, the term of this patent is extended or adjusted under 35 U.S.C. 154(b) by 159 days.

(21) Appl. No.: 15/779,883

(22) PCT Filed: Aug. 16, 2016

(86) PCT No.: PCT/US2016/047135
§ 371 (c)(1),
(2) Date: May 30, 2018

(87) PCT Pub. No.: WO2017/031100
PCT Pub. Date: Feb. 23, 2017

(65) Prior Publication Data
US 2018/0323088 A1 Nov. 8, 2018

Related U.S. Application Data (60) Provisional application No. 62/207,417, filed on Aug. 20, 2015.

(51) Int. Cl.
*B23P 9/00* (2006.01)
*A61K 47/60* (2017.01)
(Continued)

(52) U.S. Cl.
CPC ............ *A61K 47/60* (2017.08); *A61K 31/728* (2013.01); *A61K 38/08* (2013.01); *A61P 27/04* (2018.01);
(Continued)

(58) Field of Classification Search
CPC ...... A61K 47/60; A61K 38/08; A61K 31/728; H01L 24/75; H01L 24/00; H01L 21/67092; H01L 21/67132; A61P 27/04
See application file for complete search history.

(56) References Cited

U.S. PATENT DOCUMENTS 4,096,774 A * 6/1978 Kaufmann ............. B21D 28/12
83/552
5,397,423 A * 3/1995 Bantz ................... B23Q 39/042
156/350

(Continued)

FOREIGN PATENT DOCUMENTS

KR 10-2015-0065519 A 6/2015
KR 10-2015-0090422 A 8/2015

OTHER PUBLICATIONS

PCT Search Report and Written Opinion of PCT Application No. PCT/US2016/047135, dated Nov. 16, 2016, 11 pages.

*Primary Examiner* — Paul D Kim
(74) *Attorney, Agent, or Firm* — Maine Cernota & Rardin (57) ABSTRACT

Herein described is a system for the placement of dies on a substrate that uses a rotating turret carried with the die placement system to supply die placement heads necessary for the placement of various dies on a substrate, where multiple dies are to be placed, to a force application rod, thereby allowing for the rapid and efficient placement of a variety of dies on a single substrate.

20 Claims, 6 Drawing Sheets (51) Int. Cl.
  *H01L 23/00*    (2006.01)
  *H01L 21/67*    (2006.01)
  *A61P 27/04*    (2006.01)
  *A61K 31/728*   (2006.01)
  *A61K 38/08*    (2019.01)

(52) U.S. Cl.
  CPC .. *H01L 21/67092* (2013.01); *H01L 21/67132* (2013.01); *H01L 24/00* (2013.01); *H01L 24/75* (2013.01)

(56) References Cited

U.S. PATENT DOCUMENTS

| | | | |
|---|---|---|---|
| 5,487,216 A * | 1/1996 | Demarest | A61B 17/0467 |
| | | | 29/705 |
| 5,966,903 A | 10/1999 | Dudderar | |
| 8,317,077 B2 * | 11/2012 | Hwang | B23K 1/0012 |
| | | | 228/39 |
| 2005/0045914 A1 | 3/2005 | Agranat | |
| 2014/0154037 A1 | 6/2014 | Sen | |
| 2016/0089710 A1 * | 3/2016 | Sakamoto | B21D 28/125 |
| | | | 83/552 |

* cited by examiner

DIE PLACEMENT HEAD WITH TURRET

RELATED APPLICATIONS

This application is a national phase application filed under 35 USC § 371 of PCT Application No. PCT/US2016/047135 with an International filing date of Aug. 16, 2016, which claims the benefit of U.S. Provisional Application No. 62/207,417, filed Aug. 20, 2015. These applications are herein incorporated by reference in their entirety for all purposes.

FIELD

The disclosure relates to die placement, and more particularly, to a die placement head incorporating a tool-carrying turret for use in die placement, attachment and bonding operations, such as die placement on epoxy, eutectic attachment and flip-chip bonding, respectively.

BACKGROUND

The manufacture of integrated circuits (ICs) generally involves the use of complex lithographic processes to form microscopic solid-state devices and circuits in semiconductor wafers. These lithographic processes typically include forming layers of material on the wafer, patterning the layers, doping the substrate and/or the patterned layers and heat-treating (e.g., annealing) the resulting structures. These processes are then repeated to build up the IC structure. The result is a wafer containing a large number of ICs.

After the wafer is formed, it then will typically go through a sorting process. Sorting involves electrically testing each IC chip on the wafer for functionality. After sorting, the wafer is separated into individual IC chips, which are then packaged individually or in groups for incorporation onto a substrate, such as a printed circuit board (PCB).

At this stage of the process, the individual ICs are typically referred to as dies. These dies must then be placed on and fixed to specific locations on a substrate such that they become electronically and/or optically connected to other components with which they are designed to interact.

The machine responsible for placing the dies on a substrate is referred to as a die placement system, and sometimes as a "chip shooter". Such a machine typically includes an optical vision system that locates and recognizes fiducials and other alignment marks or features on the die or elements attached thereto. Information from the optical vision system relating to the position of the die relative the alignment marks allows the die to be placed on the substrate at a specific location.

During such a die placement operation, die positioning must be very precise and accurate to ensure that interconnections between the die and substrate are properly established. To this end, substrates commonly include alignment marks or "fiducials" to assist in die placement. The placement of semiconductor devices onto a substrate or a printed circuit board is generally referred to in the industry as the die placement, die attach or die bonding operation.

Similarly, when placing dies, especially dies that can vary, sometimes considerably, in size and thickness, it is critical that they be placed with a consistent, precise and accurate amount of force. For example, when placing a die on epoxy, it is critical that, after placement, the epoxy bond line thickness criteria are met. When placing very thin dies (50 um or less) in a eutectic attach process (i.e. without the use of epoxy) the impact force, if high, can lead to die cracks. The margin of error in such placement operations is quite small.

Current methods of applying forces during a die placement, attach or bonding operation usually involve compressing a spring by a set distance. Disadvantages of a spring based system include: the additional displacement, as compared to alternative designs, needed to achieve the desired force, which results in additional cycle time and inaccuracy; overshoot in displacement that is difficult, if not impossible, to prevent with such systems results in the applied force varying; and attempts to minimize overshoot by lowering the speed at which the system operates decreases the machine's productivity.

Another known method of applying force during such an operation involves bringing the die placement head to a known calibrated/taught height. One major disadvantages of this method is that, in practice, there are variations in substrate heights and die thickness that result in inconsistent force being applied to the die and substrate.

In many instances, the challenge of such operations is increased due to the need for die placement systems to place multiple dies, which are often different from one another, on a single substrate. Since different types of dies are not uniform in size or shape, the die placement head, the portion of the die placement system in contact with the dies themselves and ultimately responsible for their precise placement, is specific to each type of die to be placed. In such situations, the die placement head must be swapped during the die placement operation with one that corresponds to the next die type to be placed before the next die placement operation can proceed.

This swapping of the die placement head can be manual or automatic. Manual methods require opening of the machine by a human operator and subsequent exchange of the die placement head while automatic swapping is typically accomplished by moving the die placement head to a tool carrier and swapping out the die placement head for one corresponding to the next die to be placed. Both manual and automatic swapping of die placement heads slows down the die placement process and manual die placement head swapping also poses a significant risk of contamination, since the system must be opened for the swapping operation. While automatic swapping of die placement heads is quicker than manual die placement head swapping, it still requires that the die placement head travel a significant distance within the system, resulting in the possible loss of placement accuracy due to tracking issues such as drift and an increase in cycle time due to time spent traversing this distance.

Today, with a wide variety of high density die package designs already available, with still more being developed every day, the requirements on die placement systems are increasing. Current generation dies require die bonding equipment that can deliver precision, versatility and speed beyond what is currently available to maximize productivity while minimizing defects resulting from faulty die placement, which, considering the effort that has already gone into creating and testing dies at this point in the production process, is an especially great concern. Future generations of dies are very likely to impose even higher requirements on die placement equipment.

What is needed, therefore, are techniques for improving the accuracy, precision and consistency of die placement and the application of die placement force while accelerating the die placement process, especially where multiple dies must be placed on a single substrate.

SUMMARY

One embodiment of the present disclosure provides a system for the placement of dies on a substrate comprising: a frame; a housing fixed to the frame, the housing comprising a guide channel encompassing a force application rod, which extends from a distal end of the housing, the force application rod configured for linear motion relative to the housing and the application of linear force, a measurement device configured to measure the linear motion of the force application rod, the force application rod further comprising a die placement head holding aperture at a distal end thereof; a turret rotatably fixed to the frame comprising a rotation measuring device and a plurality of die placement head holding portions positioned substantially adjacent a periphery thereof wherein each die placement head holding portion comprises two concentric apertures, a first aperture and a second aperture, the first aperture positioned adjacent the distal end of the housing and extending fully through the turret, the second aperture positioned on the side of the turret opposite the first aperture and concentric therewith, wherein the first aperture is of a size only slightly larger than that of the force application rod and the second aperture extends only partially into the turret and wherein, upon rotation, each of the plurality of die placement head holding apertures can be brought into alignment with the force application rod; and a motor fixed to the frame and configured to rotate the turret upon activation.

Another embodiment of the present disclosure provides such a system further comprising at least one die placement head having a proximal end configured to be held in the die placement head holding aperture of the force application rod during use in a die placement operation, a central region configured to be removably retained in the second aperture of the turret upon retraction of the force application rod above the turret and a distal end including a die holding and retaining portion.

A further embodiment of the present disclosure provides such a system wherein the plurality of die placement head holding portions of the turret are configured in multiple concentric rows.

Yet another embodiment of the present disclosure provides such a system wherein the die placement head holding aperture of the force application rod further comprises magnets therein configured to retain a die placement head inserted therein.

A yet further embodiment of the present disclosure provides such a system wherein the magnets are permanent magnets.

Still another embodiment of the present disclosure provides such a system wherein the magnets are electromagnets.

A still further embodiment of the present disclosure provides such a system wherein the turret further comprises magnets configured to retain a die placement head in an aperture thereof.

Even another embodiment of the present disclosure provides such a system wherein the magnets are permanent magnets.

An even further embodiment of the present disclosure provides such a system wherein the magnets are electromagnets.

A still even another embodiment of the present disclosure provides such a system wherein the die placement head holding aperture of the force application rod is in operative communication with a controllable vacuum source.

A still even further embodiment of the present disclosure provides such a system further comprising a die placement head configured to allow vacuum to be drawn therethrough, whereby a die to be placed may be retained securely in the die placement head through the use of such vacuum.

Still yet another embodiment of the present disclosure provides such a system wherein a portion of the force application rod external to the housing further comprises a projection, wherein the projection is restricted from rotation but substantially unrestricted during normal usage against linear motion.

A still yet further embodiment of the present disclosure provides such a system wherein the projection is hollow, thereby allowing vacuum to be pulled therethrough or pressure forced therein.

Even yet another embodiment of the present disclosure provides such a system wherein the force application rod is an air piston, the guide channel is an air cylinder, and the guide channel is in communication with a vacuum or pressure source, wherein the introduction of vacuum or pressure into the guide channel results in a linear movement of or application of force to the force application rod.

An even yet further embodiment of the present disclosure provides such a system wherein the guide channel further comprises a spring configured to bias linear movement of the force application rod.

Still even yet another embodiment of the present disclosure provides such a system wherein the force application rod is of a polygonal shape and the guide channel is of a corresponding polygonal shape, whereby the polygonal shape provides resistance to rotation of the force application rod.

A still even yet further embodiment of the present disclosure provides such a system further comprising at least one voice coil which at least partially surrounds the force application rod, wherein the at least one voice coil is configured to induce linear movement of or the application of linear force into the force application rod.

Yet still even another embodiment of the present disclosure provides such a system wherein the motor produces rotational movement of the turret via a belt and pulley drive system.

A yet still even further embodiment of the present disclosure provides such a system wherein the belt is a timing belt and the pulleys are timing pulleys.

A still yet even another embodiment of the present disclosure provides such a system further comprising a hall-effect sensor, wherein the hall-effect sensor is configured to measure the location of the force application rod.

A yet still even another embodiment of the present disclosure provides such a system wherein the die placement head holding aperture is tapered, having a larger opening adjacent the distal end of the force application rod and becoming relatively narrower further from the distal end of the force application rod.

A still another yet embodiment of the present disclosure provides such a system wherein the tapered die placement head holding aperture is conical in shape.

A still yet another further embodiment of the present disclosure provides such a system further comprising at least one die placement head having a proximal end configured to be held in the tapered die placement head holding aperture of the force application rod during use in a die placement operation, a central region configured to be removably retained in the second aperture of the turret upon retraction of the force application rod above the turret and a distal end including a die holding and retaining portion.

A still yet another even further embodiment of the present disclosure provides such a system wherein vacuum or pressure held between the force application rod and an end of the housing guide channel is used as an air spring.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
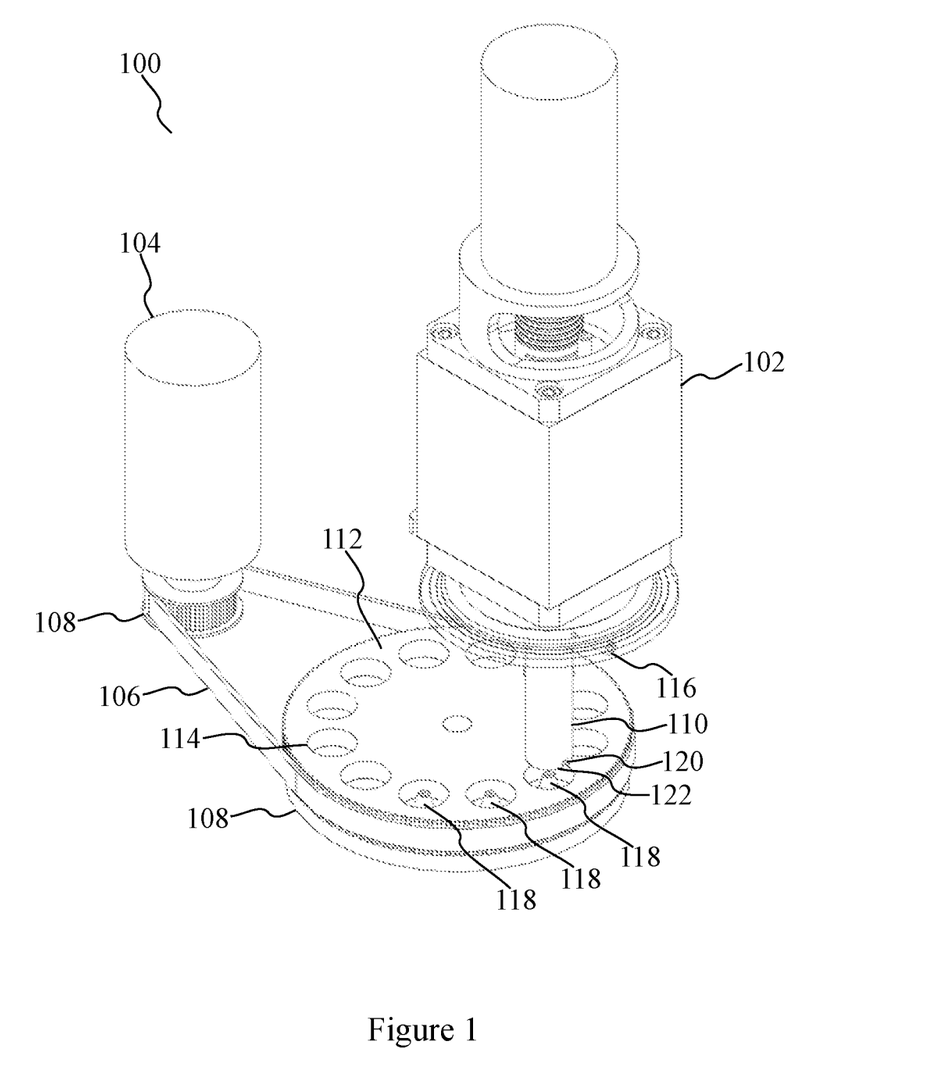
FIG. 1 is a perspective view of a die placement system wherein the die placement head of the force application rod is in an unloaded state, configured in accordance with one embodiment of the present disclosure.
Figure 2:
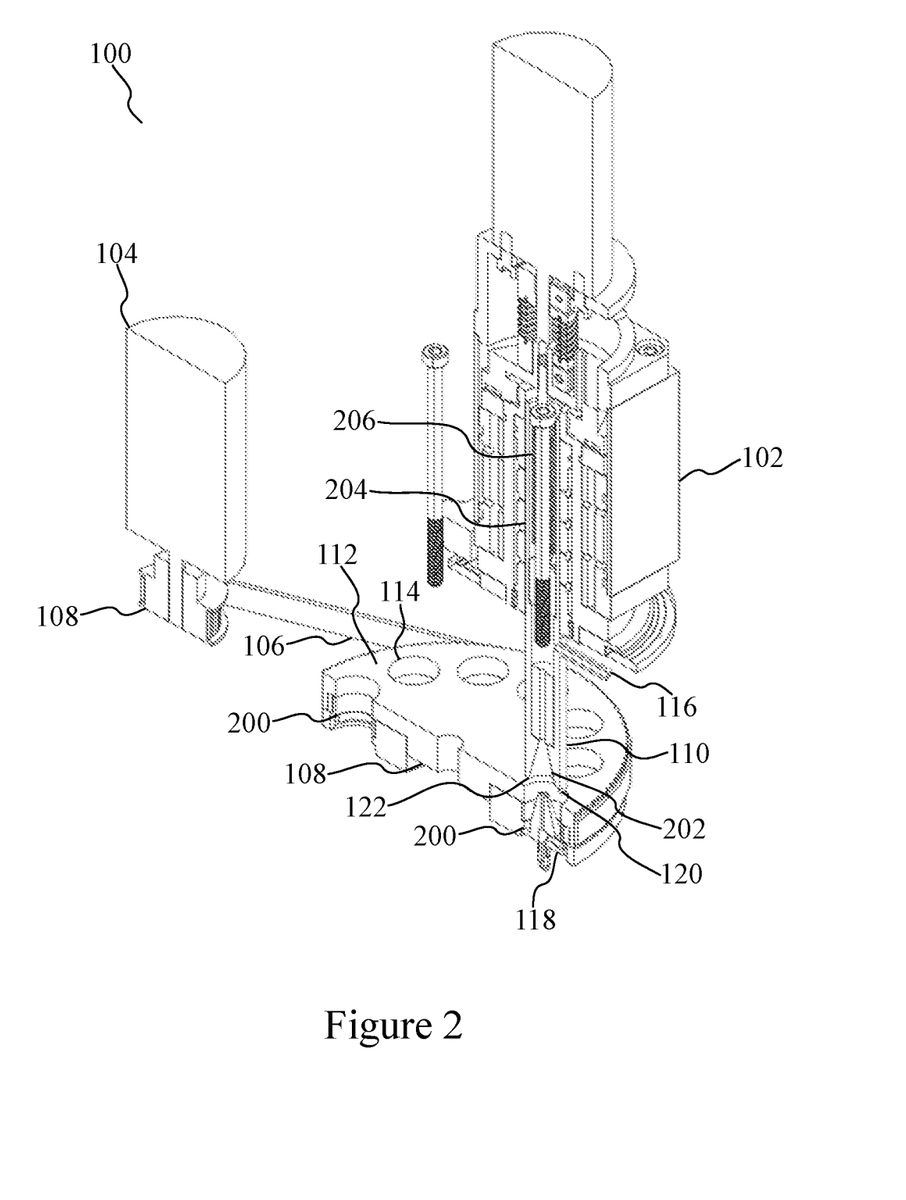
FIG. 2 is a cross-sectional perspective view of a die placement system wherein the die placement head of the force application rod is in an unloaded state, configured in accordance with one embodiment of the present disclosure.
Figure 3:
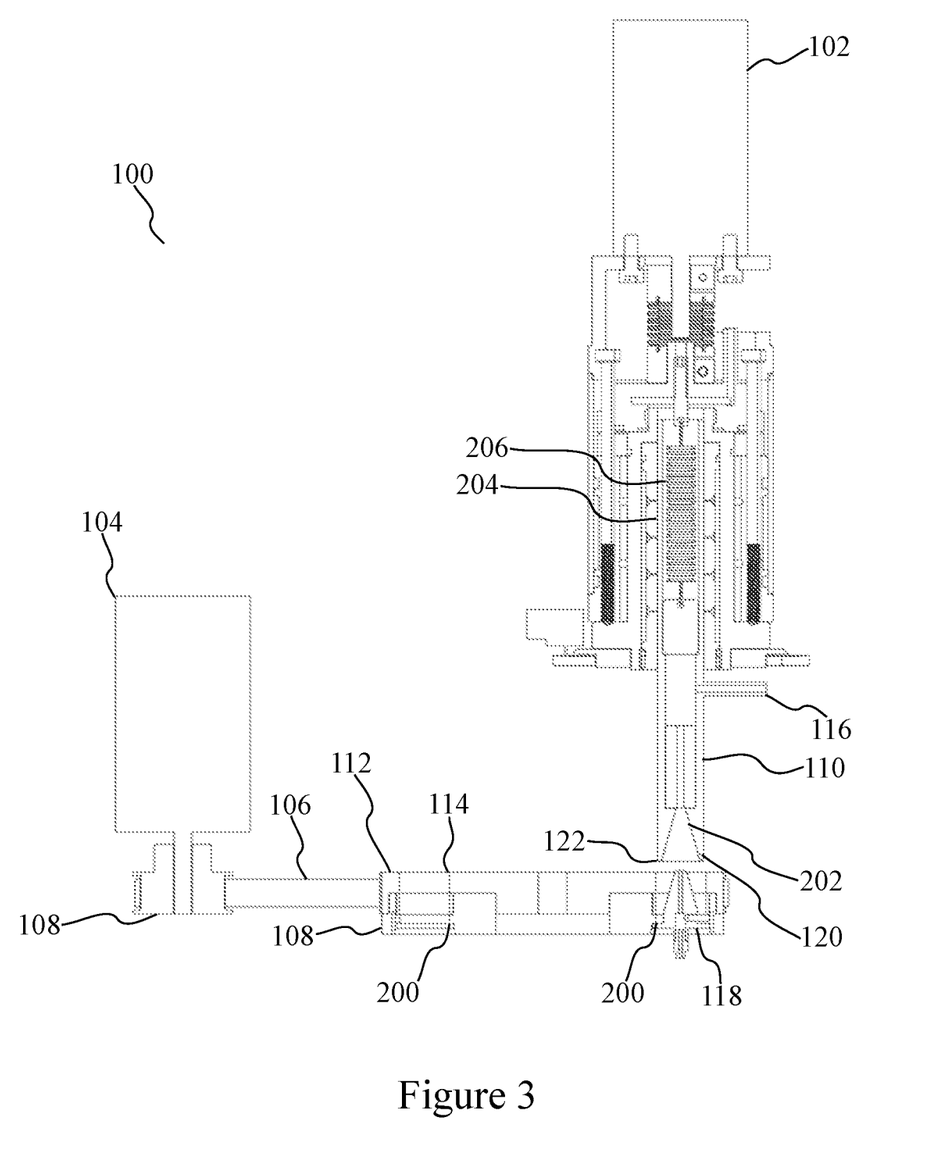
FIG. 3 is a front elevation sectional view of a die placement system wherein the die placement head of the force application rod is in an unloaded state, configured in accordance with one embodiment of the present disclosure.
Figure 4:
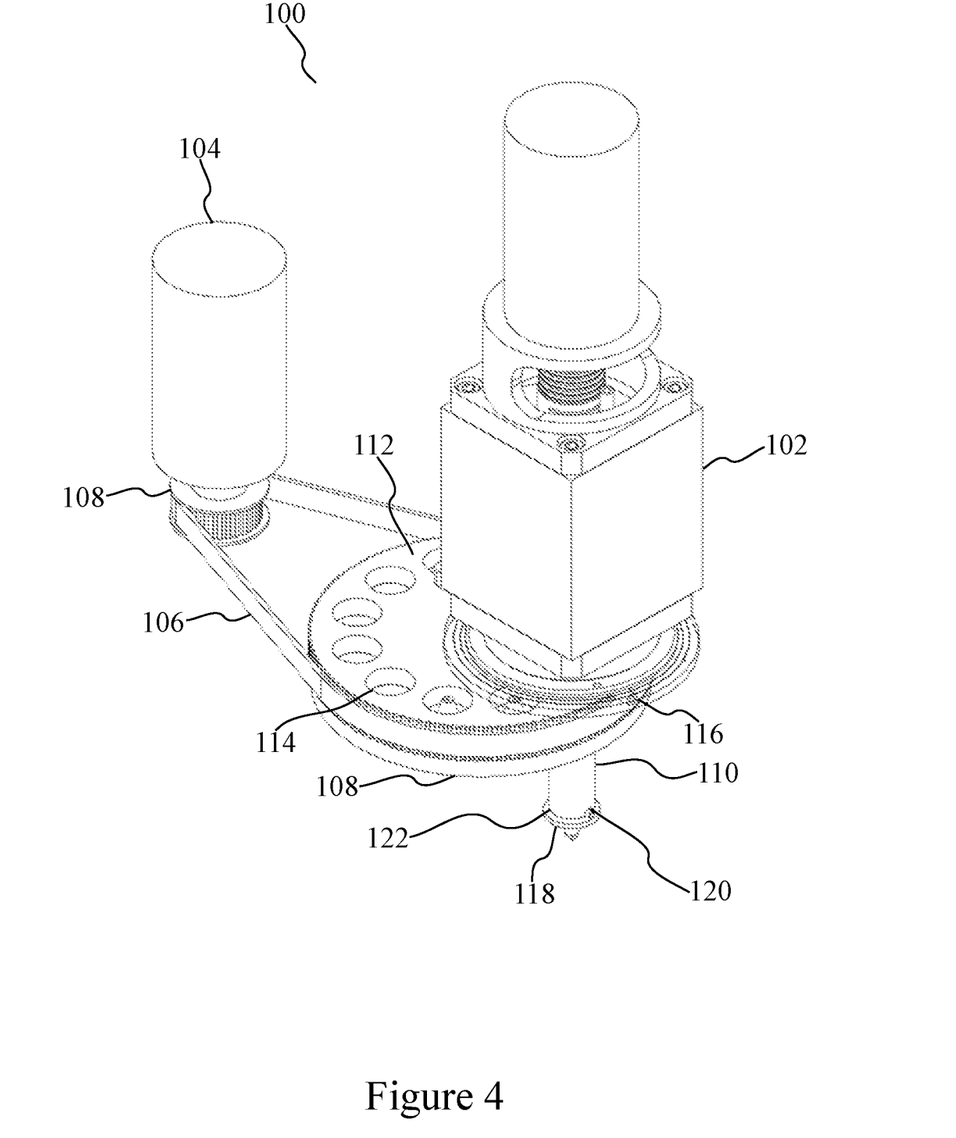
FIG. 4 is a perspective view of a die placement system wherein the die placement head of the force application rod is in a loaded state, configured in accordance with one embodiment of the present disclosure.
Figure 5:
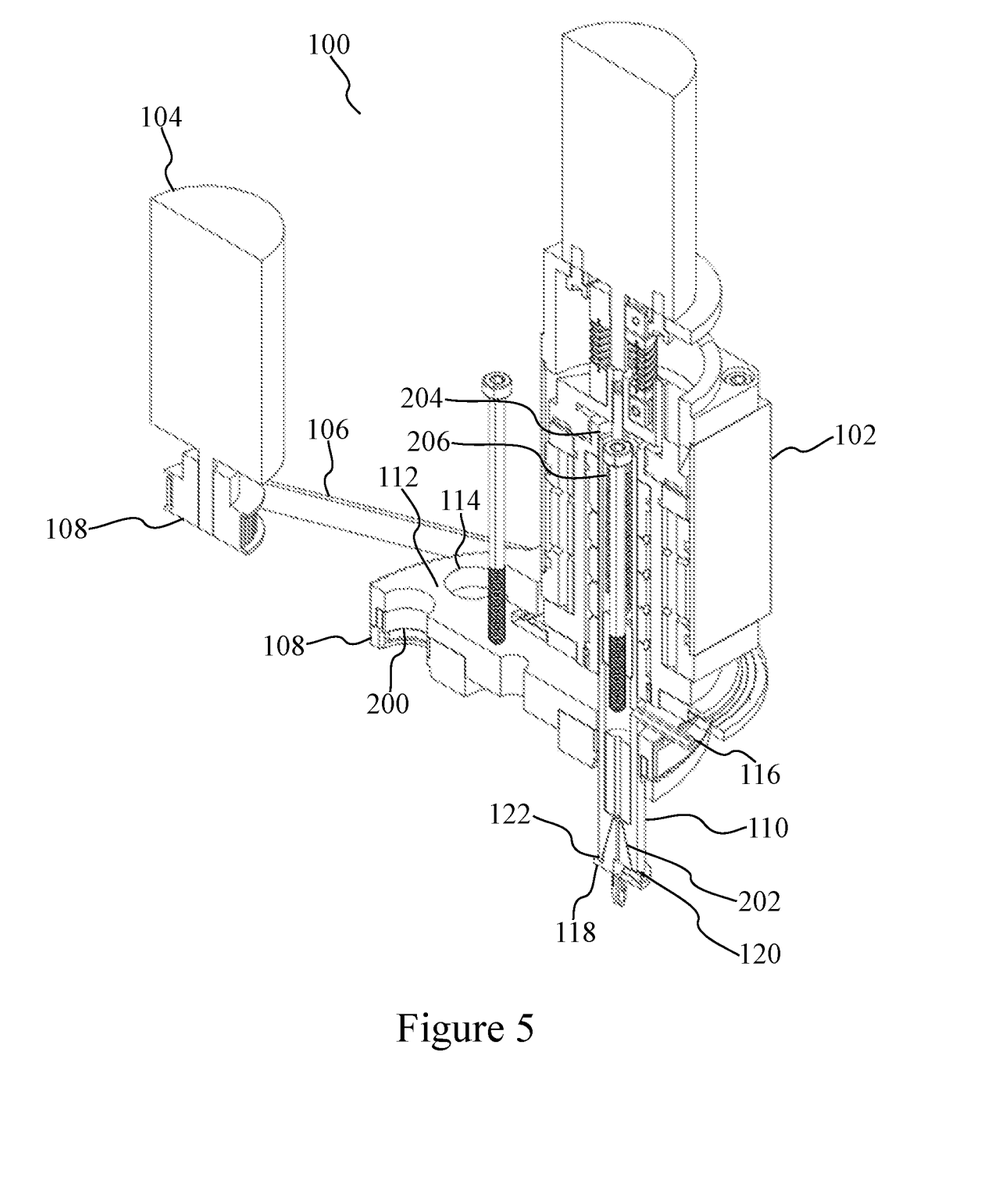
FIG. 5 is a perspective view of a die placement system wherein the die placement head of the force application rod is in a loaded state configured in accordance with one embodiment of the present disclosure.
Figure 6:
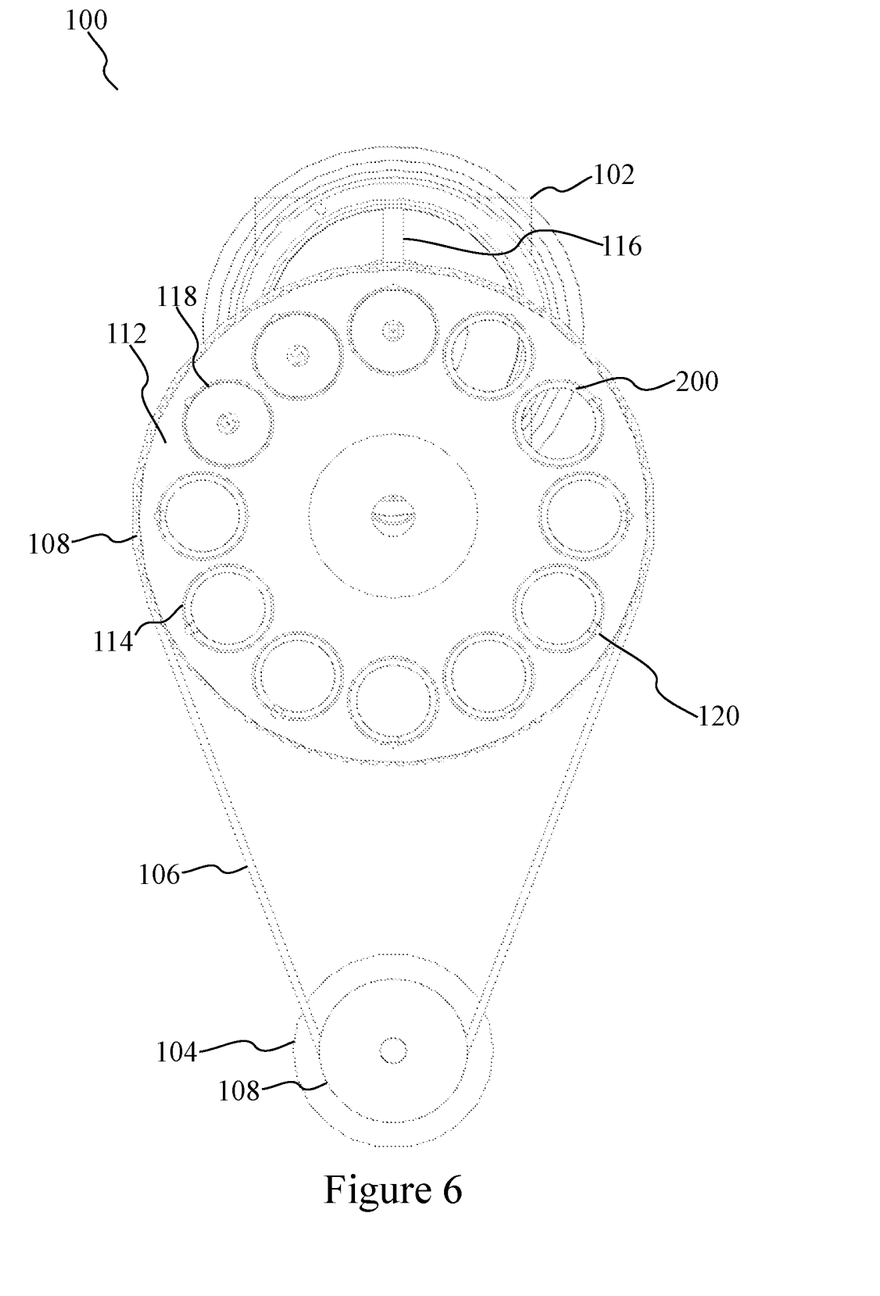
FIG. 6 is a bottom elevation view of a die placement system configured in accordance with one embodiment of the present disclosure.

In general terms, a die placement cycle comprises the following steps: 1. Determining the position of the die in 3D space using markers on the die and substrate themselves, which are generally referred to as fiducials; 2. Pickup of the die by the die placement head 118; 3. Imaging and angular or theta correction; and 4. Placement of the die onto the substrate. For the placement of multiple dies on a single substrate, steps 1-4 are repeated as necessary.

Dies may be presented for placement in various ways, such as in wafers, waffle packs, and tape & reel. Using the common case of wafer processing for an example, wafers are received, after dicing into individual dies, on a film frame. Cassettes of wafers are then fed to the machine, and one wafer is indexed into the machine for placement. In order to pick a device from the frame, an ejector pin is typically used to push the die off of the frame while the die placement head 118 lifts the die, often through the use of a vacuum. The most common approach used for component assembly is to perform the dispensing and placement operations on one machine that is commonly referred to as a die bonder.

Dies are extremely small in size, typically on the order of 10 to 15 mils in any given direction. Because of their tiny size, the mechanism for moving and controlling a tool for picking up and transferring such a die must be constructed to minimize tolerances as much as possible while maintaining high throughput to be commercially viable. The situation becomes even more challenging when multiple die types are to be placed on a single substrate. Because of the small size and non-standardized nature of dies, different tool heads, referred to as die placement heads 118, must be used for each die type.

Reduction of the cycle time for such operations while maintaining precision and accuracy is crucial to the cost-effective production of die/substrate packages. An increase in the speed at which a die placement head 118 can be changed results in an immediate improvement to the total cycle time required to perform the die placement operation. Movement of the die placement head 118 also takes time and results in a longer cycle time than if such movement could be eliminated. Also, since excessive movement of the die placement head 118 can be detrimental to accuracy, keeping such movement to a minimum can help to enhance the precision and accuracy of the die placement system 100.

The present disclosure describes an improved die placement system 100 that allows for the efficient placement of multiple die types by a single die placement system 100 during a die placement cycle, yielding improvements in cycle times and accuracy. This is accomplished through minimization of the movement of the die placement system 100 in operations involving the placement of multiple dies on a single substrate where die placement heads 118 must be swapped to accommodate differently sized dies by incorporating a die placement head 118 holding turret 112, a rotating holder for tools, into the die placement system 100. The turret 112 of such a system carries all die placement heads 118 necessary for use in a particular application, negating the need for the die placement system 100 to return to a traditional tool holder between die placement operations involving differently sized dies. In embodiments, the turret 112 may incorporate permanent magnets, electro-magnets, vacuum passages or combinations thereof to retain the die placement heads 118 when not in use. Other suitable means of retaining the die placement heads 118 within the turret 112 would be apparent to one of ordinary skill in the art.

The die placement system 100 of the present disclosure, in one embodiment, comprises a housing 102, frame, motor 104, transmission 106/108, force application rod 110, and linear measurement device. The housing 102 encompasses the force application rod 110 and linear measurement device. In embodiments, an encoder, hall-effect sensor, or other measuring device, as would be known to one of ordinary skill in the art, may be used to measure the linear travel of the force application rod 110. The frame connects the housing 102, turret 112 and motor 104, with the motor 104 operatively connected to the turret 112 by a force transmission means 106/108, to the remainder of the die bonding system, which is not shown.

In embodiments, the force transmission means 106/108 is a belt 106 and pulley 108 system. In other embodiments, the belt 106 is a timing belt 106 and the pulleys 108 are timing pulleys 108, respectively. In this case, timing belt 106 refers to a toothed belt 106 and timing pulley 108 refers to pulleys 108 having teeth that correspond to those of the timing belt 106, to prevent slippage so that the position of the components to each other, once calibrated, will be known during future operations.

The turret 112 portion of the die placement system 100, in embodiments, has the capability to hold between 15-20 separate die placement heads 118, although more or less could be held. Some embodiments utilize a single row of tool-holding apertures 114 while others incorporate multiple rows of tool-holding apertures 114 into a single turret 112. Representative embodiments of the present disclosure show the turret 112 having a circular shape; other shapes, however, could also be used without departing from the scope of the current disclosure.

Each turret 112 tool-holding aperture 114, in embodiments, may also comprise a lip 200 situated adjacent an upper edge thereof, the upper edge being considered the edge closest to the central portion of the die placement system 100. In such embodiments, the lip 200 is designed to prevent a die placement head 118 contained therein from passing through the turret 112 upon retraction of a force-application rod 110 therethrough. To function, the lip 200 must be small enough to allow the force-application rod 110 to penetrate therethrough without impeding its motion, but must also intrude into the tool-holding aperture 114 sufficiently to prevent the die placement head 118 from passing therethrough upon retraction of the force-application rod 110.

The die placement system 100 must also ensure that the die does not rotate during placement, which would prevent proper alignment. One way that this can be accomplished is through the use of an anti-rotation member 116. In one embodiment, the anti-rotation member 116 comprises a substantially perpendicular projection from the force-application rod 110 that is supported by bearings, bushings, or similar mechanical restraints that are fastened to the frame of the die placement system 100.

In embodiments, the above-described substantially perpendicular projection 116 may be hollow. Such a design allows for a vacuum to be drawn or pressure provided to other parts of the die placement system 100, or indeed any other part of the larger system to which the die placement system 100 is connected, therethrough. For example, vacuum may be supplied to the force application rod tip 122 portion of the system for secure die placement head 118 holding. In embodiments, the vacuum provided to the force application rod tip 122 is distinct from vacuum operation of the larger die placement system 100.

In other embodiments, the force application rod 110 may be of a polygonal shape corresponding to a force-application rod 110 guide channel 204 within the die placement system 100, specifically one contained within the housing 102. In still other embodiments, the force application rod 110 may utilize a square air bearing anti-rotate design built into the guide channel 204. The use of an air bearing anti-rotate offers less friction than other embodiments, allowing better repeatability under certain conditions.

In such an embodiment, as well as other embodiments not yet described, the force-application rod 110 may be an air piston and the force-application rod 110 guide channel 204 may be an air cylinder.

In still other embodiments, the position of and force applied by the force application rod 110 may be controlled by electrical means, such as through the use of a voice coil. A spring 206 internal to the housing 102 guide channel 204 may further be inserted or connected between the housing 102 and force application rod 110, residing in the guide channel 204, such that it biases the force application rod 110 to retract or extend in the absence of additional forces.

In embodiments, a back side of the die placement heads 118 may be of a shape that corresponds to a tool-holding aperture 114 of the turret 112 in which they are designed to fit. The tool-holding aperture 114 may beneficially be keyed, i.e. contain a keyway 120, such that the die placement head 118 orientation is accurately known without requiring the use of additional sensors. Similarly, the force application rod tip 122 may beneficially incorporate a keyway 120 for the same reason. In embodiments, the back side of the die placement head 118 is circular with a keyed portion corresponding to the turret 112 keyway 120, although other shapes are also considered within the scope of this disclosure.

In some embodiments, the tip 122, or tool-holding portion, of the force-application rod 110 may incorporate a tapered seat 202, proximal the turret 112 for retention of the die placement heads 118. In such embodiments, the die placement heads 118 would have a corresponding tapered portion on the side proximal the force-application rod 110, allowing for self-alignment of the interconnecting pieces of the die placement system 100. In one embodiment, the tapered seat 202 is a conical seat.

Each and every page of this submission, and all contents thereon, however characterized, identified, or numbered, is considered a substantive part of this application for all purposes, irrespective of form or placement within the application. This specification is not intended to be exhaustive or to limit the disclosure to the precise form disclosed. The particular embodiments disclosed above are illustrative only, as the application may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the application. Accordingly, the protection sought herein is as set forth in the claims below.

The invention claimed is:

1. A system for the placement of dies on a substrate comprising:
   a frame;
   a housing fixed to said frame, said housing comprising a guide channel encompassing a force application rod, which extends from a distal end of said housing, said force application rod configured for linear motion relative to said housing and the application of linear force, a measurement device configured to measure the linear motion of said force application rod, said force application rod further comprising a die placement head holding aperture at a distal end thereof;
   a turret rotatably fixed to said frame comprising a rotation measuring device and a plurality of die placement head holding portions positioned substantially adjacent a periphery of the turret, wherein each die placement head holding portion comprises two concentric apertures, a first aperture and a second aperture, said first aperture positioned adjacent the distal end of said housing and extending fully through said turret, said second aperture positioned on the side of the turret opposite said first aperture and concentric therewith, wherein said first aperture is of a size only slightly larger than that of said force application rod and said second aperture extends only partially into said turret and wherein, upon rotation, each of said plurality of die placement head holding apertures can be brought into alignment with said force application rod; and
   a motor fixed to said frame and configured to rotate said turret upon activation.

2. The system of claim 1 further comprising at least one die placement head having a proximal end configured to be held in said die placement head holding aperture of said force application rod during use in a die placement operation, a central region configured to be removably retained in said second aperture of said turret upon retraction of said force application rod above said turret and a distal end including a die holding and retaining portion.

3. The system of claim 1 wherein said plurality of die placement head holding portions of said turret are configured in multiple concentric rows.

4. The system of claim 1 wherein said die placement head holding aperture of said force application rod further comprises magnets configured to retain a die placement head inserted therein.

5. The system of claim 1 wherein said turret further comprises magnets configured to retain a die placement head in at least one of the plurality of die placement head holding portions thereof.

6. The system of claim 1 wherein said die placement head holding aperture of said force application rod is in operative communication with a controllable vacuum source.

7. The system of claim 6 further comprising a die placement head configured to allow vacuum to be drawn therethrough.

8. The system of claim 1 wherein a portion of said force application rod external to said housing further comprises a projection, wherein said projection is restricted from rotation but substantially unrestricted during normal usage against linear motion.

9. The system of claim 8 wherein said projection is hollow, thereby allowing vacuum to be pulled therethrough or pressure forced therein.

10. The system of claim 1 wherein said force application rod is an air piston, said guide channel is an air cylinder, and said guide channel is in communication with a vacuum or pressure source, wherein the introduction of vacuum or pressure into said guide channel results in a linear movement of or application of force to the force application rod.

11. The system of claim 10 wherein said guide channel further comprises a spring configured to bias linear movement of said force application rod.

12. The system of claim 10 wherein said force application rod is of a polygonal shape and said guide channel is a corresponding polygonal shape, whereby said polygonal shape provides resistance to rotation of said force application rod.

13. The system of claim 1 further comprising at least one voice coil which at least partially surrounds said force application rod, wherein said at least one voice coil is configured to induce linear movement of or the application of linear force into said force application rod.

14. The system of claim 1 wherein said motor produces rotational movement of said turret via a belt and pulley drive system, the pulley drive system comprising at least two pulleys and at least one belt.

15. The system of claim 14 wherein said belt is a timing belt and said pulleys are timing pulleys.

16. The system of claim 1 further comprising a hall-effect sensor, wherein said hall-effect sensor is configured to measure a location of said force application rod.

17. The system of claim 1 wherein said die placement head holding aperture is tapered, having a larger opening adjacent the distal end of the force application rod and becoming relatively narrower further from said distal end of said force application rod.

18. The system of claim 17 wherein said tapered die placement head holding aperture is conical in shape.

19. The system of claim 17 further comprising at least one die placement head having a proximal end configured to be held in said tapered die placement head holding aperture of said force application rod during use in a die placement operation, a central region configured to be removably retained in said second aperture of said turret upon retraction of said force application rod above said turret and a distal end including a die holding and retaining portion.

20. The system of claim 1 wherein vacuum or pressure held between said force application rod and an end of said housing guide channel is used as an air spring.

* * * * *